(12) United States Patent
Koudelka et al.

(10) Patent No.: US 7,667,831 B2
(45) Date of Patent: Feb. 23, 2010

(54) METHOD AND DEVICE FOR INSPECTING A SURFACE OF AN OPTICAL COMPONENT

(75) Inventors: Lubomir Koudelka, Shoreview, MN (US); Steven M. Arnold, Minnetonka, MN (US); Peter David Koudelka, St. Paul, MN (US); Ryan Elliot Eckman, Columbus Township, MN (US); Eric Karl Lindmark, Shoreview, MN (US)

(73) Assignee: PROMET International, Inc., Shoreview, MN (US)

( * ) Notice: Subject to any disclaimer, the term of this patent is extended or adjusted under 35 U.S.C. 154(b) by 0 days.

(21) Appl. No.: 11/937,801

(22) Filed: Nov. 9, 2007

(65) Prior Publication Data

US 2008/0074676 A1 Mar. 27, 2008

Related U.S. Application Data

(63) Continuation of application No. 11/046,530, filed on Jan. 28, 2005, now Pat. No. 7,312,859.

(60) Provisional application No. 60/540,476, filed on Jan. 30, 2004.

(51) Int. Cl.
*G01N 21/00* (2006.01)
(52) U.S. Cl. ..................... 356/73.1
(58) Field of Classification Search ............... 356/73.1, 356/237.2, 485, 496, 511–514, 600; 382/108, 382/312–313
See application file for complete search history.

(56) References Cited

U.S. PATENT DOCUMENTS

| | | | |
|---|---|---|---|
| 5,004,205 A * | 4/1991 | Brown et al. ............... 248/476 |
| 5,179,419 A | 1/1993 | Palmquist et al. | |
| 5,459,564 A | 10/1995 | Chivers | |
| 5,535,002 A | 7/1996 | Csipkes et al. | |
| 5,543,915 A | 8/1996 | Csipkes et al. | |
| 5,600,439 A | 2/1997 | Csipkes et al. | |
| 5,636,020 A | 6/1997 | Csipkes et al. | |
| 5,862,250 A | 1/1999 | Csipkes et al. | |
| 5,898,494 A | 4/1999 | Csipkes | |
| 5,917,595 A | 6/1999 | Norland et al. | |
| 5,973,784 A * | 10/1999 | Szwaykowski et al. ...... 356/495 |
| 6,052,505 A | 4/2000 | Bice et al. | |
| 6,215,555 B1 | 4/2001 | Chivers | |
| 6,466,310 B2 * | 10/2002 | Nguyen et al. ............. 356/73.1 |
| 6,736,702 B2 | 5/2004 | Minami | |
| 6,786,650 B2 | 9/2004 | Dean, Jr. et al. | |
| 6,831,738 B2 | 12/2004 | Rogers et al. | |

(Continued)

*Primary Examiner*—Tarifur Chowdhury
*Assistant Examiner*—Tara S Pajoohi
(74) *Attorney, Agent, or Firm*—Leanne Taveggia Farrell; Westman, Champlin & Kelly, P.A.

(57) ABSTRACT

The present invention provides an inspection system for inspecting a surface of an optical specimen. The inspection system includes an optical testing device having a main body and an optical axis. The optical testing device includes an optical imaging system housed in the main body. The optical imaging system includes imaging components for acquiring a microscope visual image and for acquiring at least one interference fringe image of the surface of the optical specimen. The optical testing device also includes a translational mechanism housed in the main body and configured to allow linear movement of the optical imaging system and to prevent off-axis movement of the optical imaging system.

17 Claims, 10 Drawing Sheets

U.S. PATENT DOCUMENTS

| | | |
|---|---|---|
| 6,954,274 B2 | 10/2005 | Sasaki et al. |
| 2002/0109831 A1 | 8/2002 | Van Nguyen et al. |
| 2002/0131754 A1* | 9/2002 | Kaiser et al. ............... 385/137 |
| 2003/0048435 A1 | 3/2003 | Nguyen et al. |
| 2003/0053043 A1 | 3/2003 | Nguyen et al. |
| 2003/0128939 A1 | 7/2003 | Nguyen et al. |

* cited by examiner

METHOD AND DEVICE FOR INSPECTING A SURFACE OF AN OPTICAL COMPONENT

The present application is a continuation of and claims priority of U.S. patent application Ser. No. 11/046,530, filed Jan. 28, 2005 which is based on and claims the benefit of U.S. provisional patent application Ser. No. 60/540,476, filed Jan. 30, 2004, the contents of which is hereby incorporated by reference in their entirety.

FIELD OF THE INVENTION

The present invention relates to an optical testing device. More particularly, the present invention relates to an optical testing device used for inspection of optical specimens.

BACKGROUND OF THE INVENTION

To join two fibers or fiber optic connectors together, the quality of a fiber endface or fiber connector endface needs to meet certain standards to maximize coupling efficiency and ensure proper operation of the fiber or fiber connector. Generally, a fiber endface or fiber connector endface has a desirable geometry or topography as well as an acceptable surface quality. A desirable surface geometry and acceptable surface quality is usually achieved through an optical polishing process and tested by one or more special optical instruments to verify that the endface meets certain standards.

Different optical instruments have been employed to inspect the endface of a fiber or fiber connector. Examples include optical microscopes and interferometric techniques. Optical microscopes magnify undesirable surface defects. Interferometric techniques utilize principles of optical interference to generate a fringe pattern representing the surface profile being inspected. These optical instruments, however, tend to be large, expensive and require a great amount of time to inspect an endface surface. These limitations make it difficult for users of polishing mechanisms to efficiently test and retest fiber or fiber connector endfaces.

For example, to inspect a surface of an endface using optical instruments known in the art, the surface should be precisely aligned with respect to the optical instrument. In general, high precision alignment stages are used to manipulate, align and focus the test surface. Manipulation and alignment of a fiber optic or fiber connector endface can be difficult if the initial position of the testing surface deviates from its nominal position. Furthermore, the existence of a multi-axis adjustment mechanism used to align the test surface increases complexity, cost of the instrument and introduces an inherent need to frequently readjust the system. Most optical instruments used for inspecting fiber or fiber connector endfaces are fairly large, bench-top instruments designed for static laboratory use. The size and weight of these devices make them impractical for portable use.

SUMMARY OF THE INVENTION

The present invention provides an inspection system for inspecting a surface of an optical specimen. The inspection system includes an optical testing device having a main body and an optical axis. The optical testing device includes an optical imaging system housed in the main body. The optical imaging system includes imaging components for acquiring a microscope visual image and for acquiring an interference fringe image of the surface of the optical specimen. The optical testing device also includes a translational mechanism housed in the main body and configured to allow linear movement of the optical imaging system along the optical axis and to prevent off axis movement of the optical imaging system.

The present invention further provides a method of inspecting a surface of an optical component. The method includes providing a portable optical testing device configured to receive and inspect an optical specimen while the optical specimen is attached to a different optical processing system. A magnified visual image of the surface of the optical specimen is acquired and a surface defect analysis is performed on the magnified visual image of the optical specimen. In addition, at least one fringe image of the surface of the optical specimen is acquired and a surface topography analysis is performed on the at least one fringe image of the optical specimen.

DETAILED DESCRIPTION OF THE PREFERRED EMBODIMENTS

Although embodiments of the present invention will be described in the context of testing an endface surface of optical fibers or fiber connectors, the present invention is applicable to other types of microscopic optical surfaces, such as lens arrays and other suitable surfaces.

Figure 1:
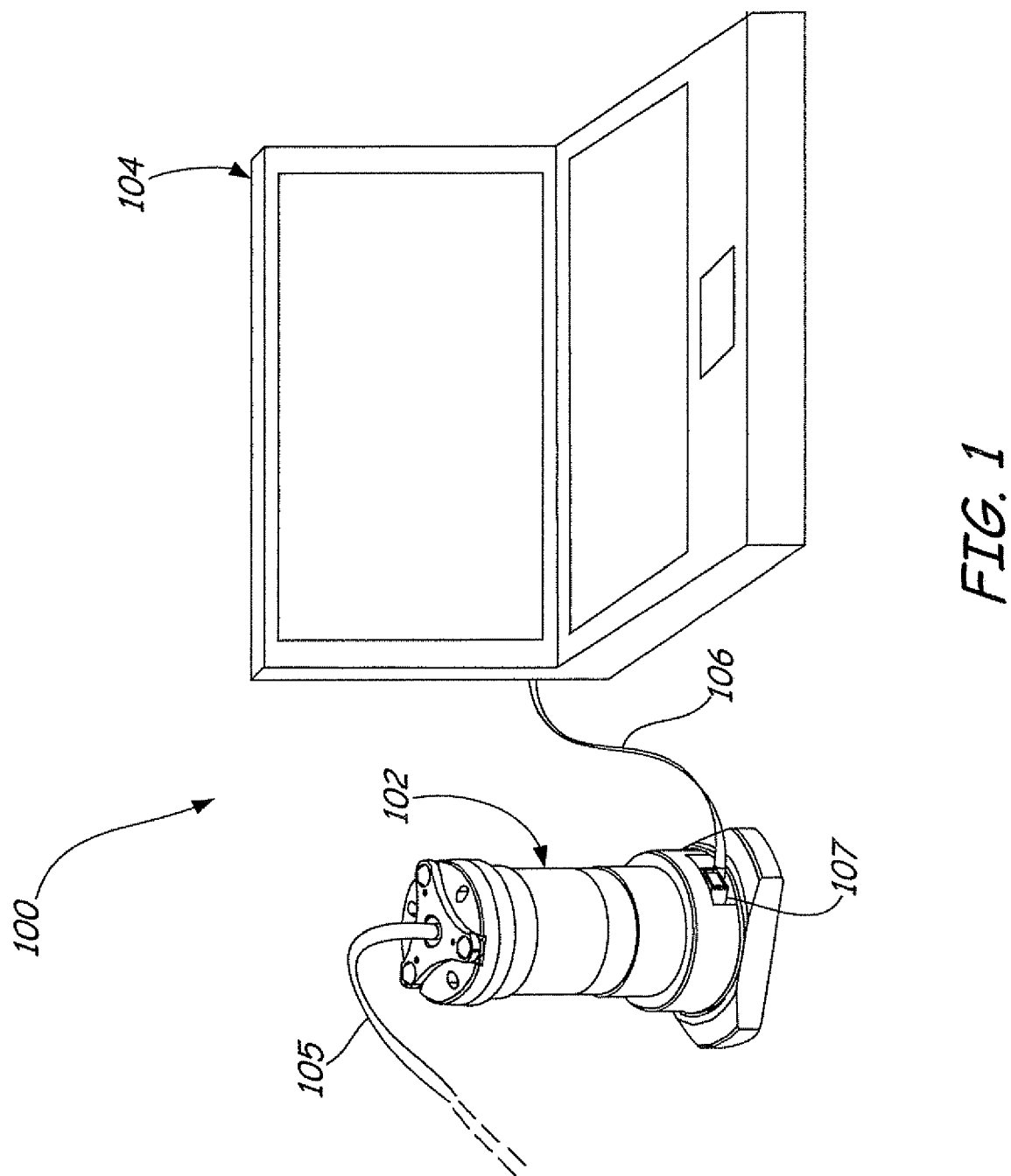
FIG. 1 illustrates a perspective view of an inspection system in accordance with an embodiment of the present invention.

FIG. 1 is a perspective view of an inspection system 100 in accordance with an embodiment of the present invention. Inspection system 100 includes an optical testing device 102 coupled to a computing device 104 preferably by a cable 106.

Optical testing device 102 is configured to receive and fixedly secure an optical specimen 105, such as an optical fiber or fiber connector endface, for inspection. Computing device 104 includes software configured to display measurement and inspection results and to initiate various electrical functions of optical testing device 102. Optical testing device 102 includes an interface 107 adapted to communicate with computing device 104. In one embodiment, interface 107 can be a Universal Serial Bus (USB) 2.0 interface. Such an interface allows optical testing device 102 to operate without an external power supply. Power can be supplied to optical testing device 102 through cable 106 and interface 107 from computing device 104. It should be noted that optical testing device 102 is not limited to any particular type of interface 107 nor any particular type of power supply. For example, interface 107 can be adapted to receive wireless signals from computing device 104 as well as include other types of interface configurations. In addition, power can be supplied to optical testing device 102 by a storage battery or other type of device.

Figure 2:
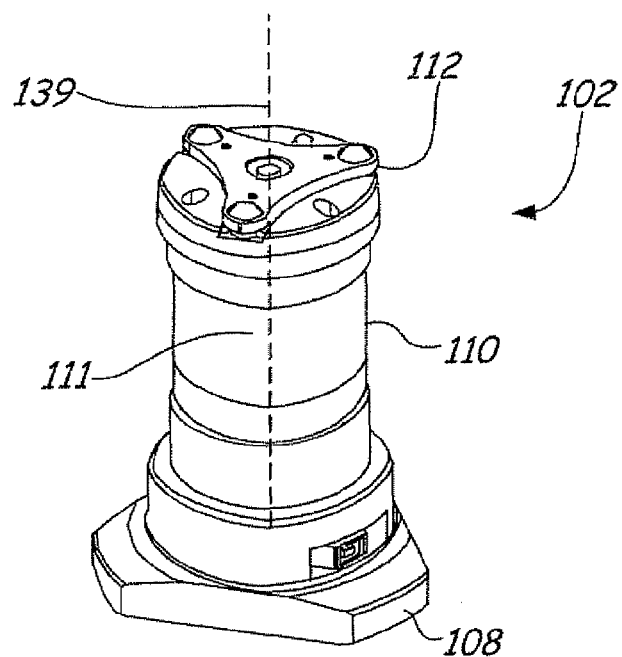
FIG. 2 illustrates an enlarged perspective view of an optical testing device in accordance with an embodiment of the present invention.

FIG. 2 illustrates an enlarged perspective view of optical testing device 102. Optical testing device 102 includes a base 108, a main body 110 and a kinematic interface 112. Main body 110 is centered about an optical axis 139. However, those skilled in the art should recognized that optical axis 139 can be placed in other positions with respect to main body 110. Base 108 is a removable base and supports main body 110 in an upright direction. When base 108 is attached to main body 110, optical testing device 102 can be supported on a level surface. Main body 110 has a slender shape that includes a grip portion 111 such that a user can easily grip and carry optical testing device 102 for portable use. Although FIG. 2 illustrates main body 110 as a cylindrical body, it should be noted that other shapes can be implemented. As illustrated in FIG. 2, kinematic interface 112 is preferably a detachable assembly located near the object plane (i.e. the area where the optical specimen is attached to the optical testing device) and configured to receive and retain an optical specimen, such as optical specimen 105 illustrated in FIG. 1, along optical axis 139. Kinematic interface 112 will be discussed in more detail with respect to FIG. 13.

Main body 110 houses a plurality of interconnected electrical components and a plurality of interconnected imaging components. For example, main body 110 includes a microprocessor. The microprocessor is used in conjunction with a camera, such as an area array detector, cable 106 (FIG. 1) and computing device 104 (FIG. 2). The microprocessor controls the function of and reports data from optical testing device 102.

Figure 3:
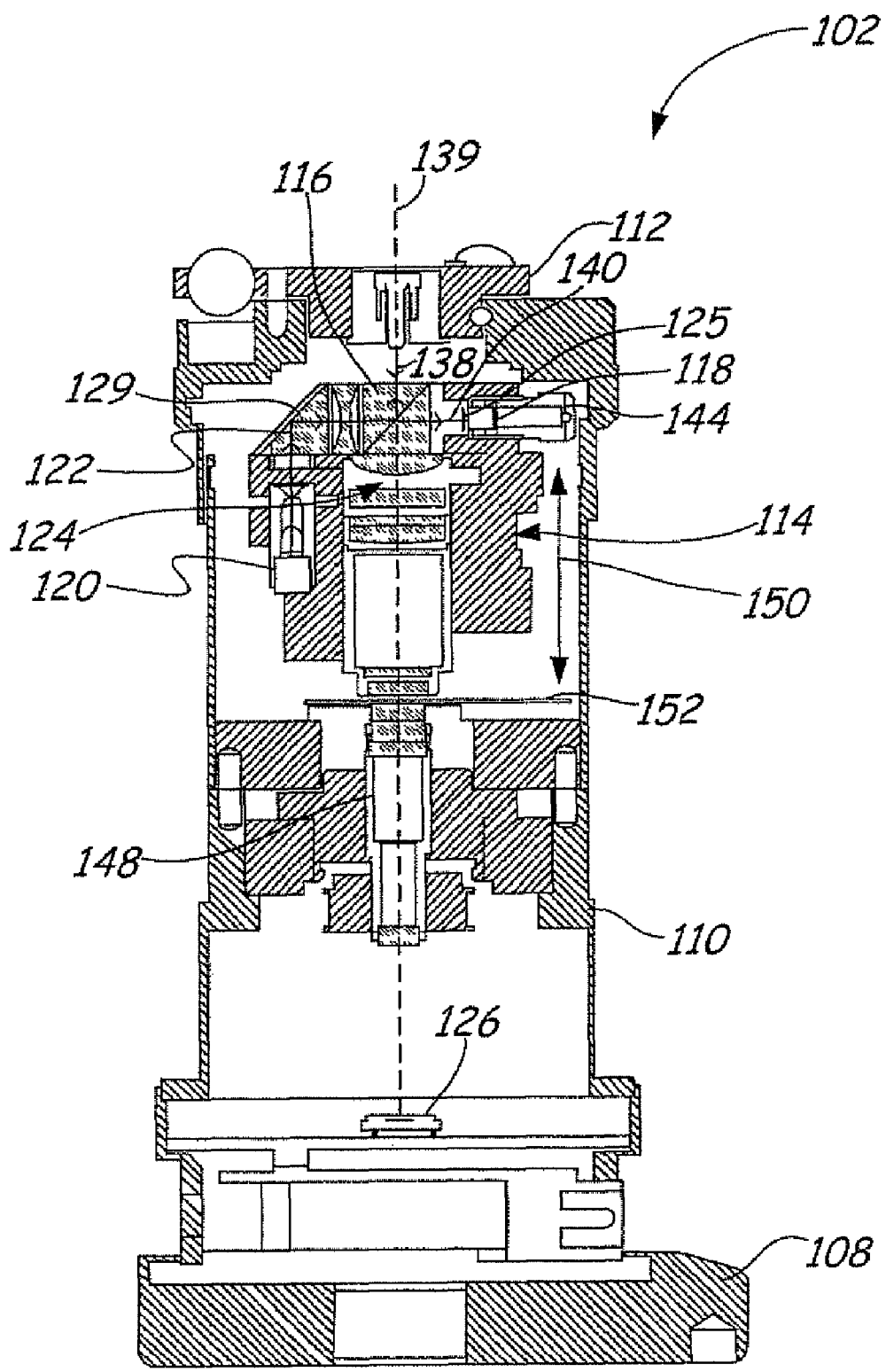
FIG. 3 illustrates a sectional view of an optical testing device in accordance with an embodiment of the present invention.

FIG. 3 illustrates a sectional view of optical testing device 102 in accordance with an embodiment of the present invention. More specifically, FIG. 3 illustrates a sectional view of base 108, main body 110 and kinematic interface 112 of optical testing device 102. Main body 110 includes optical imaging system 114. Optical imaging system 114 includes imaging components bonded together with an optical compliant adhesive such that optical testing device 102 is robust and durable. Optical imaging system 114 is capable of operating in two distinct modes. Optical imaging system 114 uses imaging components to perform or operate in a microscope visual mode and also to perform or operate in an interferometric measurement mode.

The imaging components of optical imaging system 114 are arranged in accordance with a Michelson Interferometer configuration. In a microscopic visual mode, optical testing device 102 acquires a two-dimensional magnified image of the surface of the optical specimen (i.e. microscope visual image). In an interferometric measurement mode, optical testing device 102 acquires at least one interference fringe image to produce a three-dimensional surface model or topographical image of the surface of the optical specimen. Imaging components of optical imaging system 114 include a beamsplitter 116, a reference mirror 118, an optical source or sources 120, illumination optics 122 and imaging optics 124.

During microscope visual mode operation, optical source or sources 120 produce a beam of light 129 that passes through illumination optics 122 towards beamsplitter 116. For example, optical source or sources 120 can be an LED or a plurality of LEDs. Beamsplitter 116 can be any type of optical component that splits a beam of light into two or more optical paths. In one embodiment, beamsplitter 116 can be a flat glass plate having a coating on one side. In another embodiment and as illustrated in FIG. 3, beamsplitter 116 can be a cube having two prisms fitted together. Those skilled in the art should recognize that beamsplitter 116 can include other types of configurations that are not explicitly described. Beamsplitter 116 is discussed in further detail in accordance with FIG. 6. At beamsplitter 116, beam 129 is split into beam 138 and beam 140. A shutter 125, operated by an actuator 127 (illustrated in FIG. 10), is actuated into a closed position. In one embodiment, but not by limitation, actuator 127 can be a solenoid. Shutter 125 blocks beam 140 from reflecting off of reference mirror 118. Beam 138 follows an optical path along an optical axis 139 of optical testing device 102 to illuminate the surface of the optical specimen. Imaging optics 124 are used to relate the image of the surface of the optical specimen onto an area array detector 126.

The device 102, as illustrated in FIGS. 1-3, has a rather small dimension. In particular, but not by limitation, device 102 includes a height that is approximately 150 mm and a diameter that is less than 200 mm. For example, the diameter of device 102 can be approximately 70 mm. In addition, device 102 is rather light-weight. In particular, but not by limitation, device 102 has a weight that is less than 2.25 kg. For example, device 102 can be approximately 630 g.

In one embodiment of the present invention, optical testing device 102 acquires a magnified image from area array detector 126 to be viewed by a user. In this embodiment, the user can subjectively determine if the surface of the optical specimen is in compliance with specific requirements or criteria such that further processing is unnecessary. For example, when the optical specimen is an endface of a fiber or fiber connector, the user subjectively determines if the endface needs further polishing or cleaning.

Figure 4:
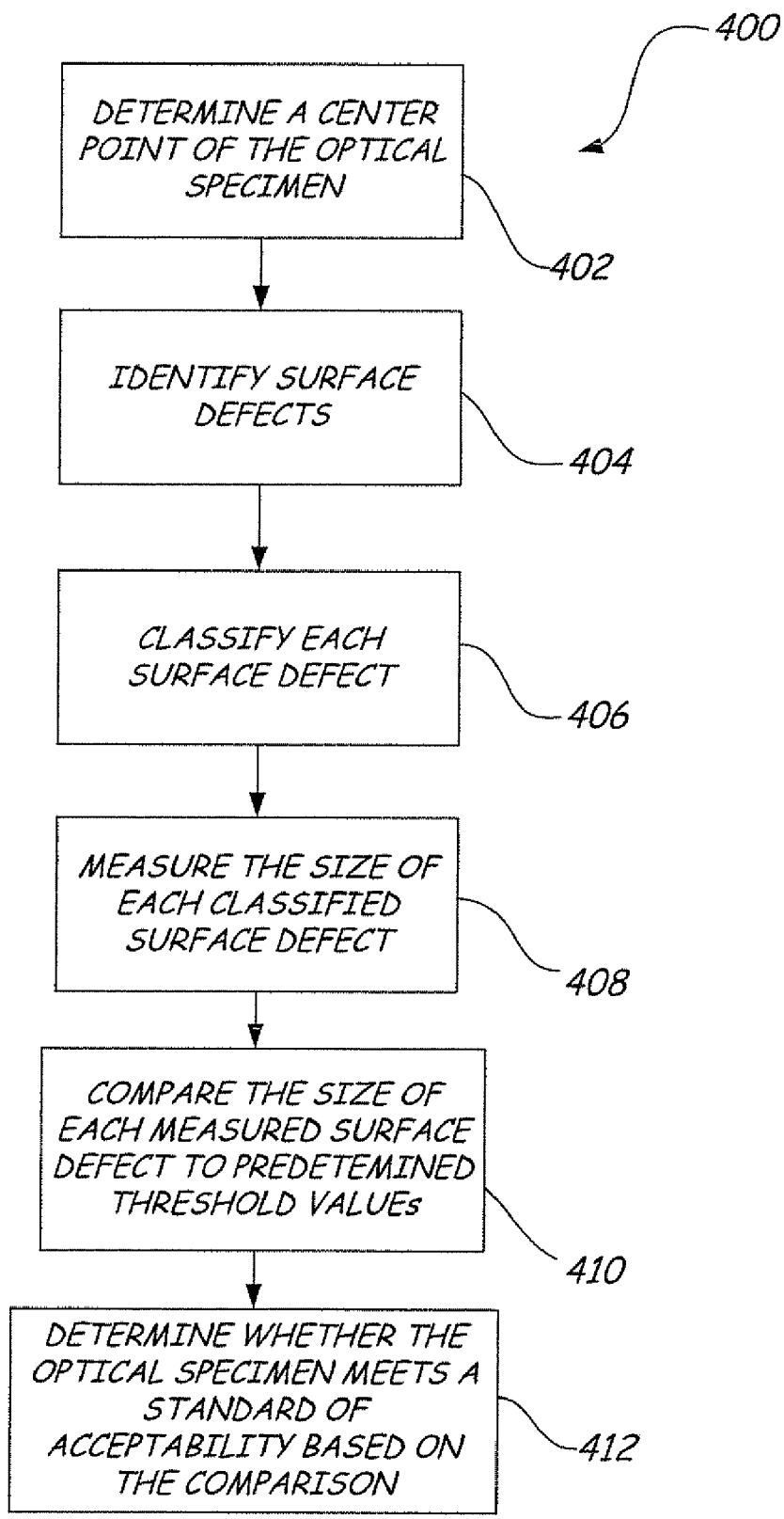
FIG. 4 is a flowchart illustrating steps associated with processing a magnified image in accordance with an embodiment of the present invention.

In another embodiment of the present invention, optical testing device 102 acquires a magnified image from area array detector 126 to be assessed by computing device 104. In this embodiment, the user can use image processing software located in computing device 104 to make objective decisions about defects on the surface of the optical specimen. FIG. 4 is a flowchart 400 illustrating steps associated with processing a magnified image acquired by optical testing device 102.

Figure 5:
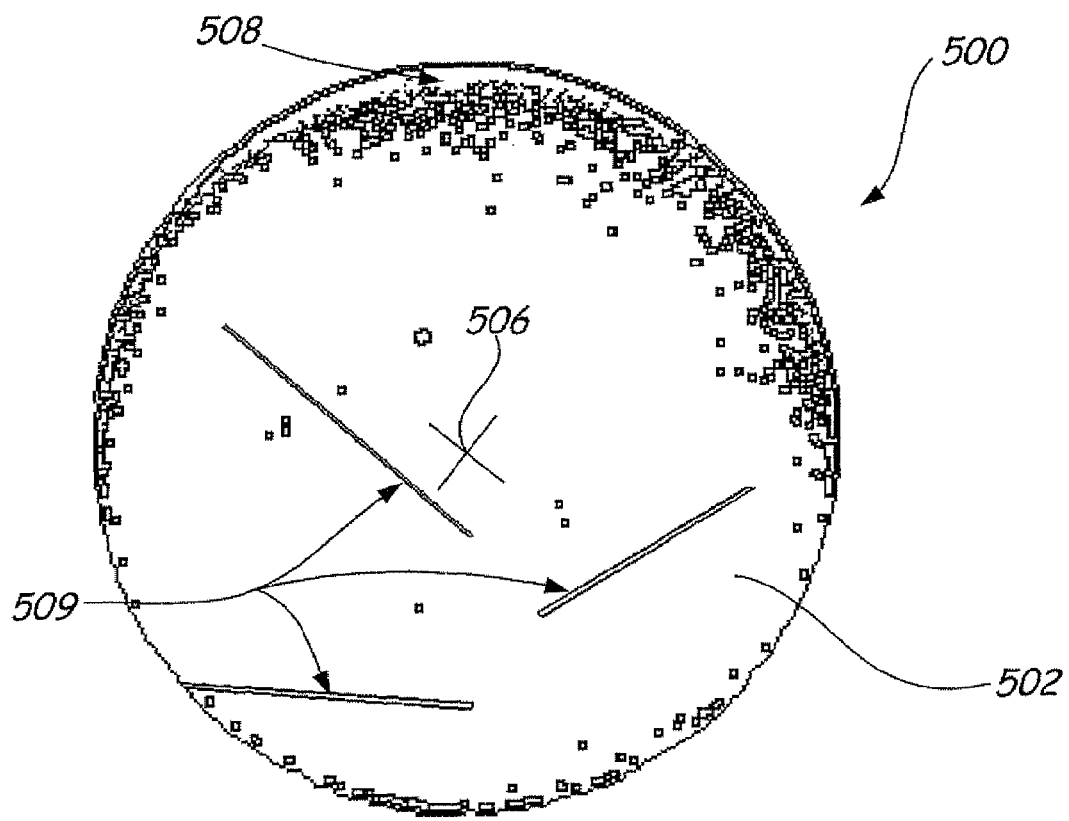
FIG. 5 illustrates an example of a magnified image in accordance with an embodiment of the present invention.

At block 402, the image processing software determines a center point of the surface of the optical specimen. The center point of the surface of the optical specimen is found by locating the circular edge of the optical specimen and applying an image processing algorithm. FIG. 5 is an example of a magnified image of a surface 502 of an optical specimen 500. FIG. 5 illustrates the designation of a center point 506. At block 404, the image processing software identifies surface defects that are located on the surface 502 of optical specimen 500. At block 406, each surface defect is classified. The image processing software can classify a surface defect as a particle, a chip or a scratch. A particle is a piece of matter that protrudes above the surface 502 of optical specimen 500. A chip or dig is an area where a portion of the optical specimen is missing or is uneven with the remaining portion of the specimen. A scratch is a long, thin chip. FIG. 5 illustrates surface defects, such as chips or digs 508 and scratches 509, on surface 502. In addition, the image processing software can determine the width of epoxy is ferrule. A large epoxy width can indicate that the diameter of the fiber is too small.

At block 408, the image processing software measures the size of each classified surface defect. For example, image processing software measures the width, length and area of the surface defects. At block 410, the image processing software compares the sizes of each surface defect to predetermined threshold values. These threshold values can be values as specified by a standard of acceptability. For example, the standard or criterion of acceptability can be commonly accepted standards such as international standards. Examples of international standards include standards from the Telecommunication Industry Association (TIA), the International Electrotechnical Commission (IEC), and/or the Telcordia standards. At block 412, the image processing software determines whether the optical specimen meets the standard of acceptability based on the comparison. If the optical specimen does not meet the standard of acceptability, then the optical specimen is further processed and retested. For example, when the optical specimen is a fiber or fiber connector, the fiber or fiber connector endface is further polished, cleaned and retested.

Figure 6:
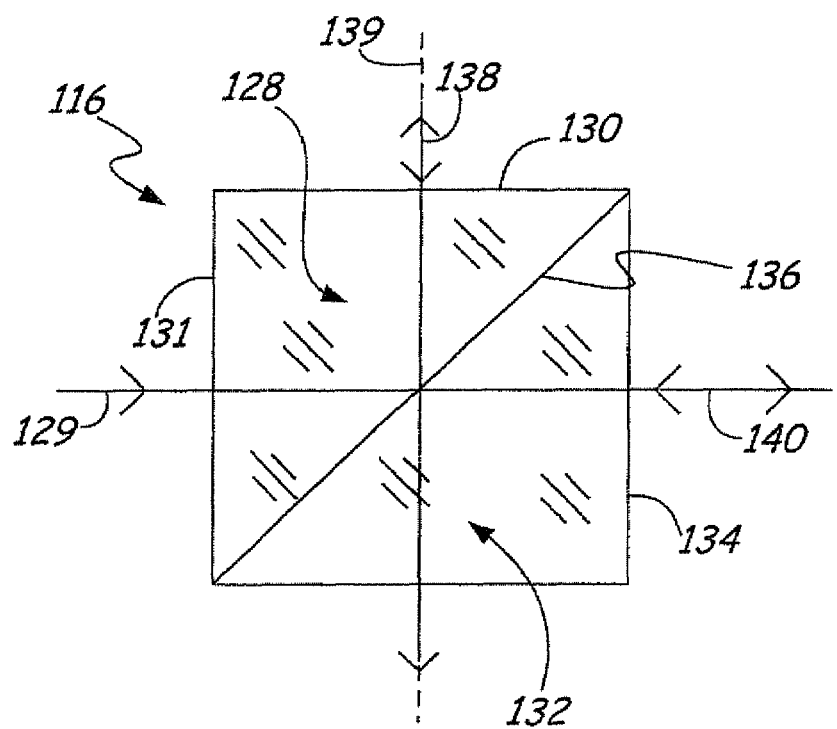
FIG. 6 illustrates a plan view of a beamsplitter in accordance with an embodiment of the present invention.

With reference back to FIG. 3, during operation in the interferometric measurement mode, optical source or sources 120 produce beam of light 129 that is diffused and passed through illumination optics 122. Illumination optics 122 directs beam 129 towards beamsplitter 116. FIG. 6 illustrates an enlarged plan view of beamsplitter cube 116 as it relates to optical paths of optical imaging system 114 during operation in an interferometric measurement mode. Beamsplitter cube 116 includes a first prism 128 having a first edge 130 and a second edge 131. Beamsplitter cube 116 also includes a second prism 132 having an edge 134. The first and second prisms 128 and 132, typically made of glass, are aligned and adhered together with an optical compliant adhesive at hypotenuse 136. Beam 129, as emitted from optical source 120 and illuminated by illumination optics 122, enters beamsplitter cube 116 at second edge 131 of prism 128. At hypotenuse 136, a portion 138 of beam 129 is reflected through first edge 130 of first prism 128 along optical axis 139 towards the test surface of the optical specimen. The remaining portion 140 of beam 129 travels through edge 134 of second prism 132 towards reference mirror 118.

First and second prisms 128 and 132 are assembled and aligned such that there is approximately a zero optical path distance difference. For example, in FIG. 3, the alignment and arrangement of beamsplitter 116 creates two similar optical paths. Specifically, the optical distance that beam 138 travels through prism 128, from hypotenuse 136 to first edge 130, is approximately the same as the optical distance beam 140 travels through prism 132 from hypotenuse 136 to edge 134. The two optical paths each have a length that is within about 1.0 microns from each other.

Referring both to FIGS. 3 and 6, beam 138 is reflected off of a surface of an optical specimen that is mounted to optical testing device 110 by kinematic interface 112 and back through first edge 130 of prism 128 towards hypotenuse 136. In interferometric measurement mode, shutter 125, operated by the actuator (illustrated in FIG. 10), is actuated into an open position. Shutter 125 allows beam 140 to reflect off of reference mirror 118 and back through edge 134 of prism 132 towards hypotenuse 136. Reference mirror 118, controlled by computing device 104 (FIG. 1), provides phase shifting capability on beam 140 for high-resolution three-dimensional surface geometry measurements. A piezoelectric element 144 can induce a phase shift in beam 140 by moving reference mirror 118. For example, piezoelectric element 144 can expand axially upon application of a voltage to actuate reference mirror 118. Those skilled in the art should recognize that other means can be used to achieve a phase shift. Instant Phase Measuring Interferometry techniques and Spatial Center techniques are examples that utilize hardware and mathematics, respectively.

At beamsplitter 116, beams 138 and 140 optically interfere or recombine and, under the correct circumstances, form interference fringes. The recombined beam or interference fringes are imaged by imaging optics 124 onto area array detector 126 for image capture and viewing. As illustrated in FIG. 3, imaging optics 124 include a plurality of lenses. After imaging optics 124 image the interference fringes, area array detector 126 creates an intensity profile of each fringe pattern for digitizing and conversion to a digital image.

Figure 8:
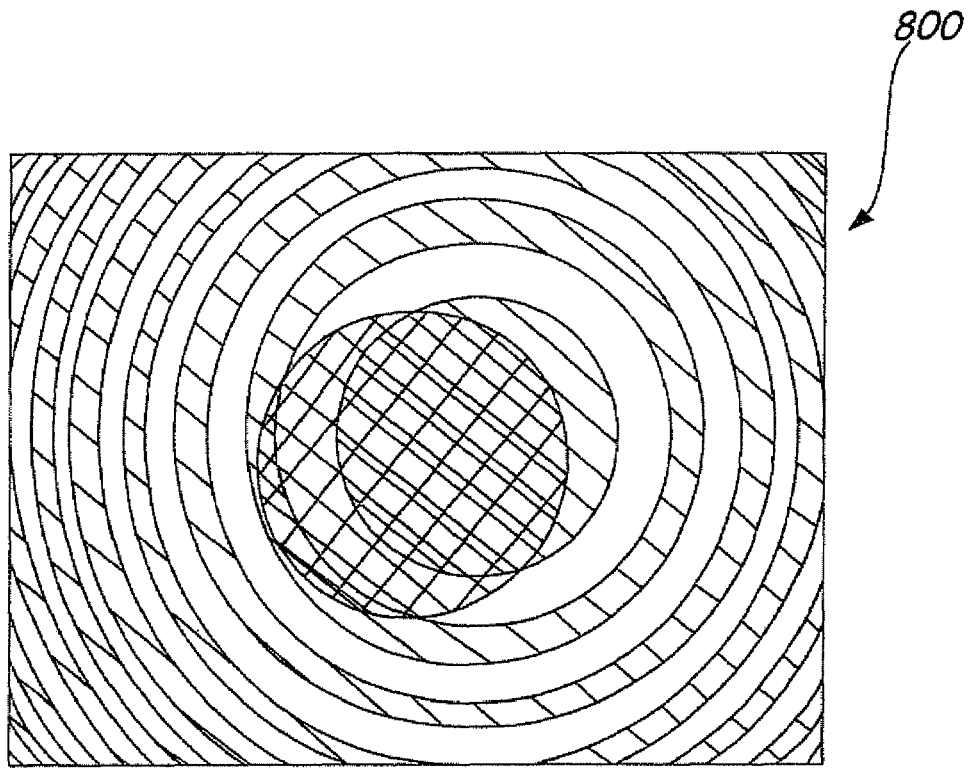
FIG. 8 illustrates an example of a fringe image in accordance with an embodiment of the present invention.
Figure 7:
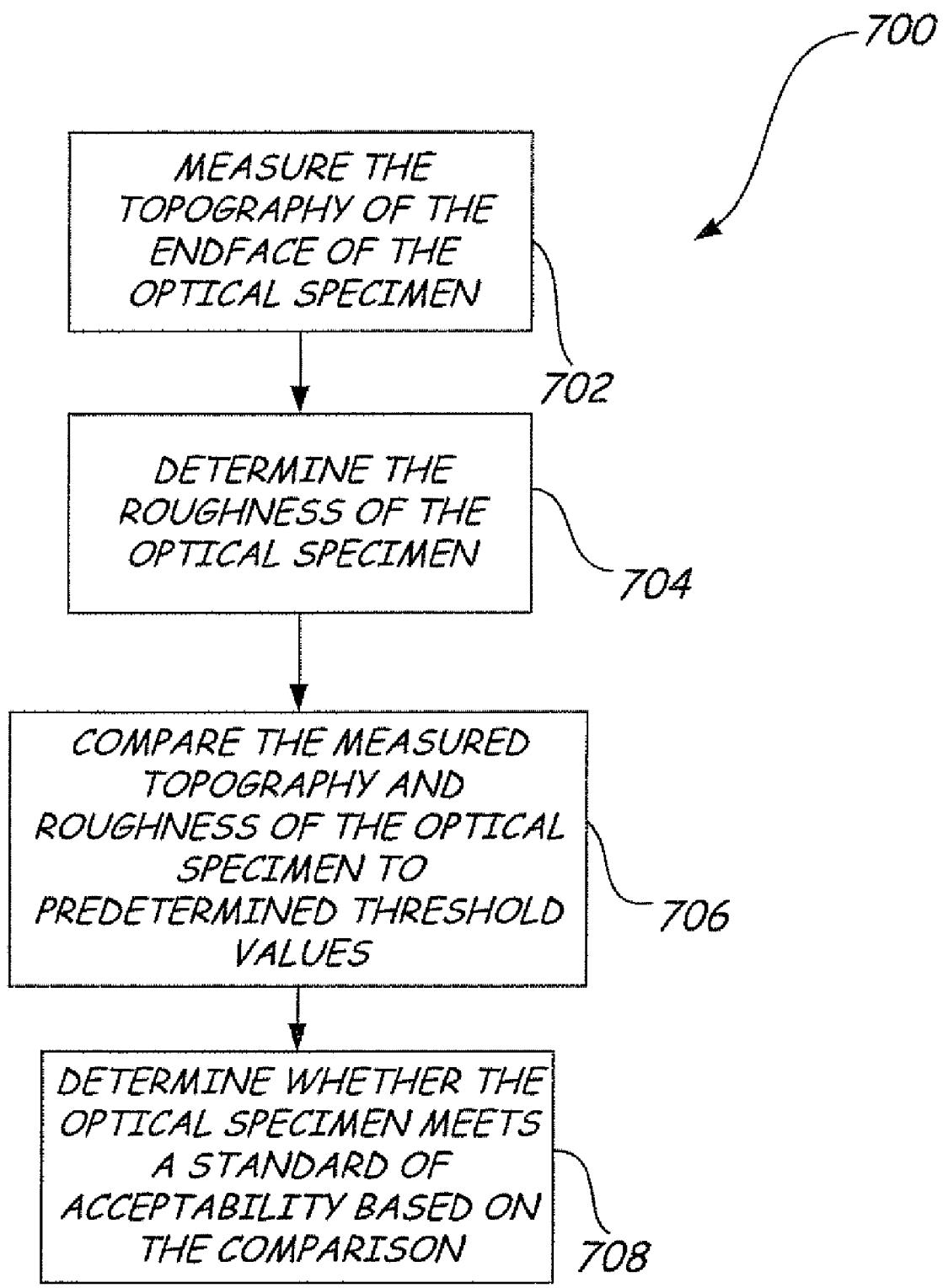
FIG. 7 is a flowchart illustrating steps associated with processing at least one fringe image in accordance with an embodiment of the present invention.

Optical testing device 102 sends the fringe image data to computing device 104 via cable 106 for fringe image processing. A user can use fringe image processing software in computing device 104 to make objective decisions related to the topography of the endface of the optical specimen. FIG. 7 is a flowchart 700 illustrating steps associated with processing a fringe image acquired by optical testing device 110 in accordance with an embodiment of the present invention. FIG. 8 illustrates an example fringe image 800 in accordance with an embodiment of the present invention.

Figure 9:
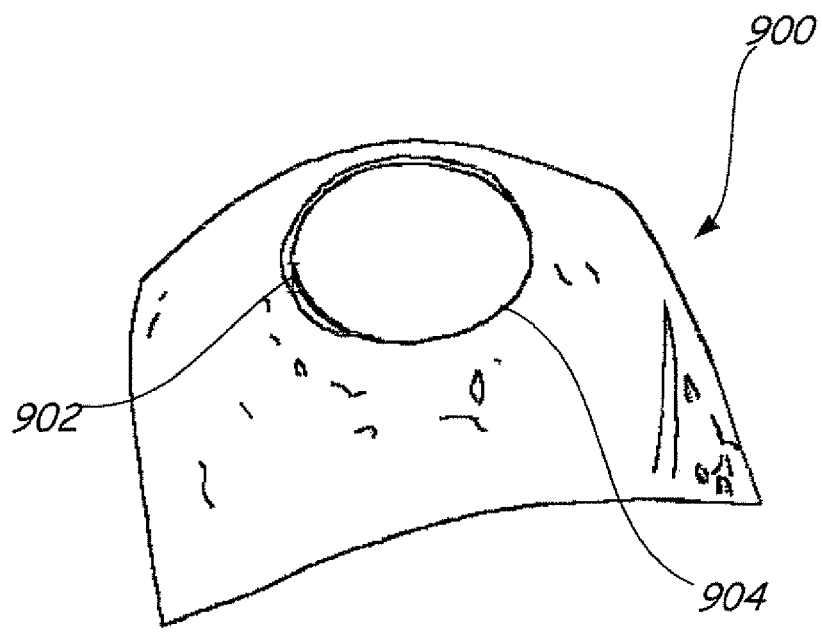
FIG. 9 illustrates an example of a topographical image that is generated based on an acquisition of at least one fringe image in accordance with an embodiment of the present invention.

At block 702, the image processing software measures the shape of the endface of the optical specimen. For example, a fiber connector endface, that is a fiber glued into a ferrule, needs to have a certain roundness, an apex that coincides with the center of the fiber and a certain amount of protrusion of the fiber with respect to the ferrule such that the fiber connector endface can make proper optical contact with other fiber connector endfaces. FIG. 9 illustrates an example of a topographical image 900 that is generated based on the at least one fringe image 800 in accordance with an embodiment of the present invention. Topographical image 900 illustrates fiber height 902 and the radius of curvature or roundness 904. At block 704, the image processing software determines the roughness of the optical specimen. For example, the roughness determination can indicate the presence of a particle on the surface of the optical specimen. At block 706, the image processing software compares the shape measurements and roughness determination to predetermined threshold values. These threshold values are values specified by standards of acceptability. For example, the standards of acceptability can be commonly accepted standards such as international standards. Examples of international standards include standards from the Telecommunication Industry Association (TIA), the International Electrotechnical Commission (IEC), and/or the Telcordia standards. At block 708, the image processing software determines whether the optical specimen meets the standards of acceptability based on the comparison. If the optical specimen does not meet these standards, then the optical specimen is further processed and retested. For example, when the optical specimen is a fiber or fiber connector, the fiber or fiber connector endface is further polished, cleaned and retested.

With reference to FIG. 3, imaging optics 124 of optical testing device 110 can be configured in a plurality of optical magnifications. For example, the magnification can be selected from a plurality of settings, such as 7×, 10×, 12×, and 20×. The magnifications are preferably selected with a turret device 148. Multiple fixed focal length elements are radially located about turret device 148. Turret device 148 is mechanically rotated such that upon each rotation a different set of fixed focal length optics are placed along optical axis 139. It should be noted that the rotation of turret device 148 can be actuated manually or actuated automatically via electrical signals received from computing device 104. Turret device 148 can also include a turret sensor (not shown). The turret sensor senses the magnification position of turret device 148 such that when optical testing device 102 is acquiring images the magnification is known. Therefore, optical imaging system can easily vary magnifications of the surface of the optical specimen being imaged on area array detector 126.

In addition, optical imaging system 114 includes the ability to adjust the focus of an image. Since the optical specimen is fixedly received (without any manipulation) by kinematic interface 112, optical imaging system 114 compensates the variation in height of the optical specimen and optimizes image quality of the surface of the optical specimen. To make adjustments, optical imaging system 114 is linearly translated along optical axis 139 in directions 150 with a translational mechanism while the optical specimen remains stationary. In one embodiment, the translational mechanism includes a plurality of shafts and bearings. In another embodiment, and as illustrated, the translational mechanism is a flex mechanism 152. Flex mechanism 152 is illustrated in detail in FIGS. 10-12.

Figure 11:
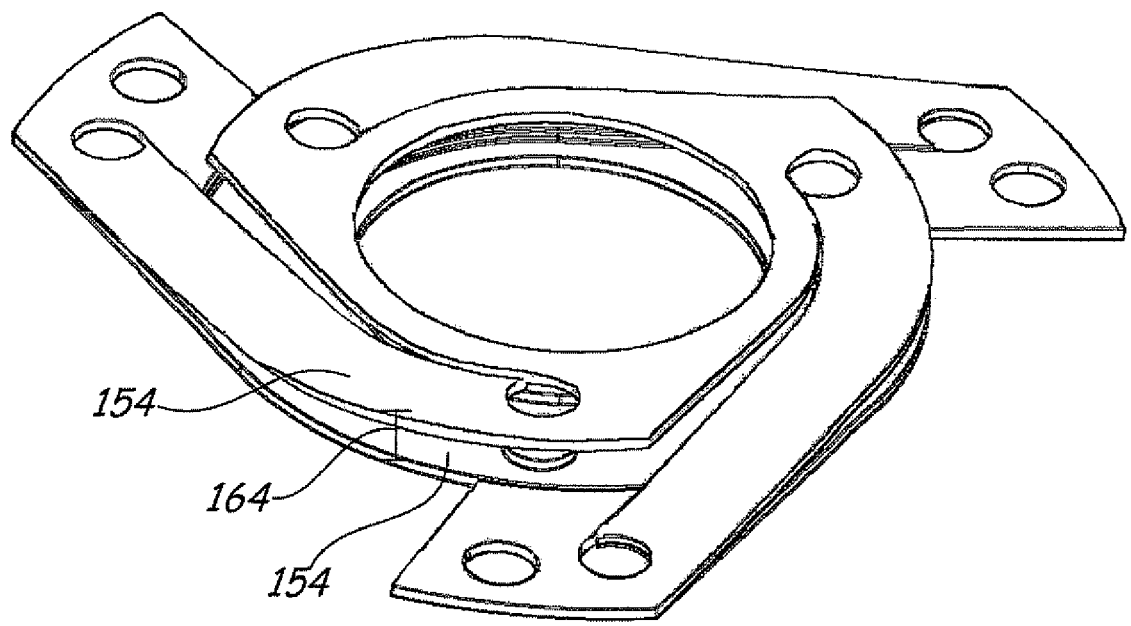
FIG. 11 illustrates a perspective view of a flexible plate in a non-deformed position and a deformed position in accordance with an embodiment of the present invention.
Figure 10:
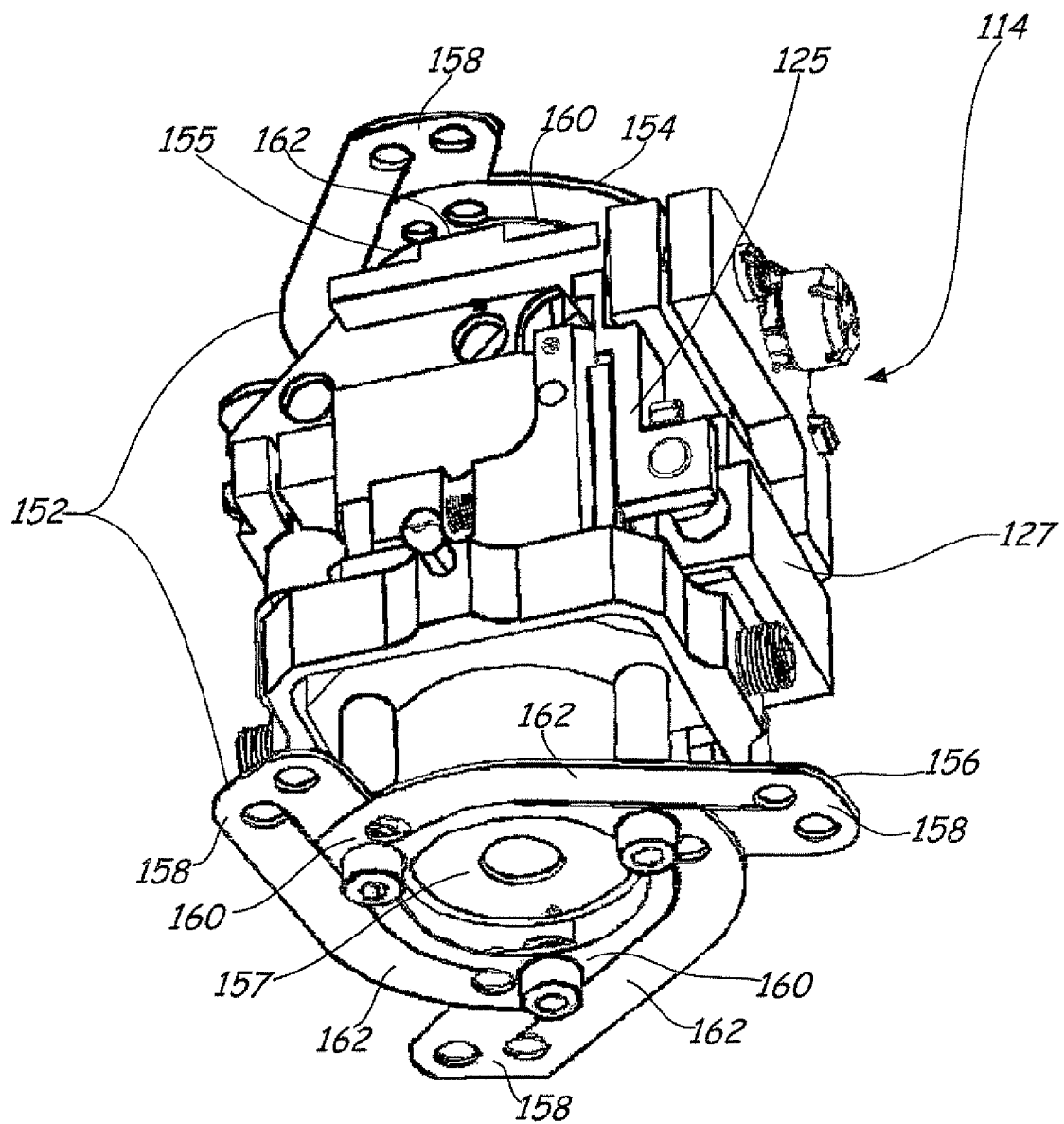
FIG. 10 illustrates a perspective view of an optical imaging system and a translational mechanism in accordance with an embodiment of the present invention.

FIG. 10 is a perspective view of optical imaging system 114 and flex mechanism 152 in accordance with an embodiment of the present invention. Flex mechanism 152 includes a first flexible plate 154 positioned at a first end 155 of optical imaging system 114 and a second flexible plate 156 positioned at a second end 157 of optical imaging system 114. First and second flexible plates 154 and 156 are flat, spring elements. For example, first and second flexible plates 154 and 156 can be made of a spring steel. However, those skilled in the art should recognize that other types of metallic and non-metallic materials that have similar properties can be used. Each flexible plate 154 and 156 includes an outer portion 158 that is configured for attachment to main body 110 (FIG. 3) of optical testing device 102 (FIG. 3) and an inner portion 160 that is configured for attachment to optical imaging system 114. Outer portion 158 is connected to inner portion 160 by a plurality of wings 162, of which three are shown. A motor (illustrated in FIG. 12), located in optical testing device 102 and preferably controlled by computing device 104, provides an axial force (in direction 150 illustrated in FIG. 3) to flexible plates 154 and 156. It should be noted, however, that a manually applied axial force can also be used to move flexible plate 154 and 156. Under this axial force, flexible plates 154 and 156 equally deform. FIG. 11 illustrates flexible plate 154 in both a non-deformed state as well as in a fully deformed state. The deformed state provides a linear motion to optical imaging system 114 over a range 164. Range 164 is approximately 3 mm. It should be noted, however, that range 164 can include other values depending on the amount of translation that is needed.

Figure 12:
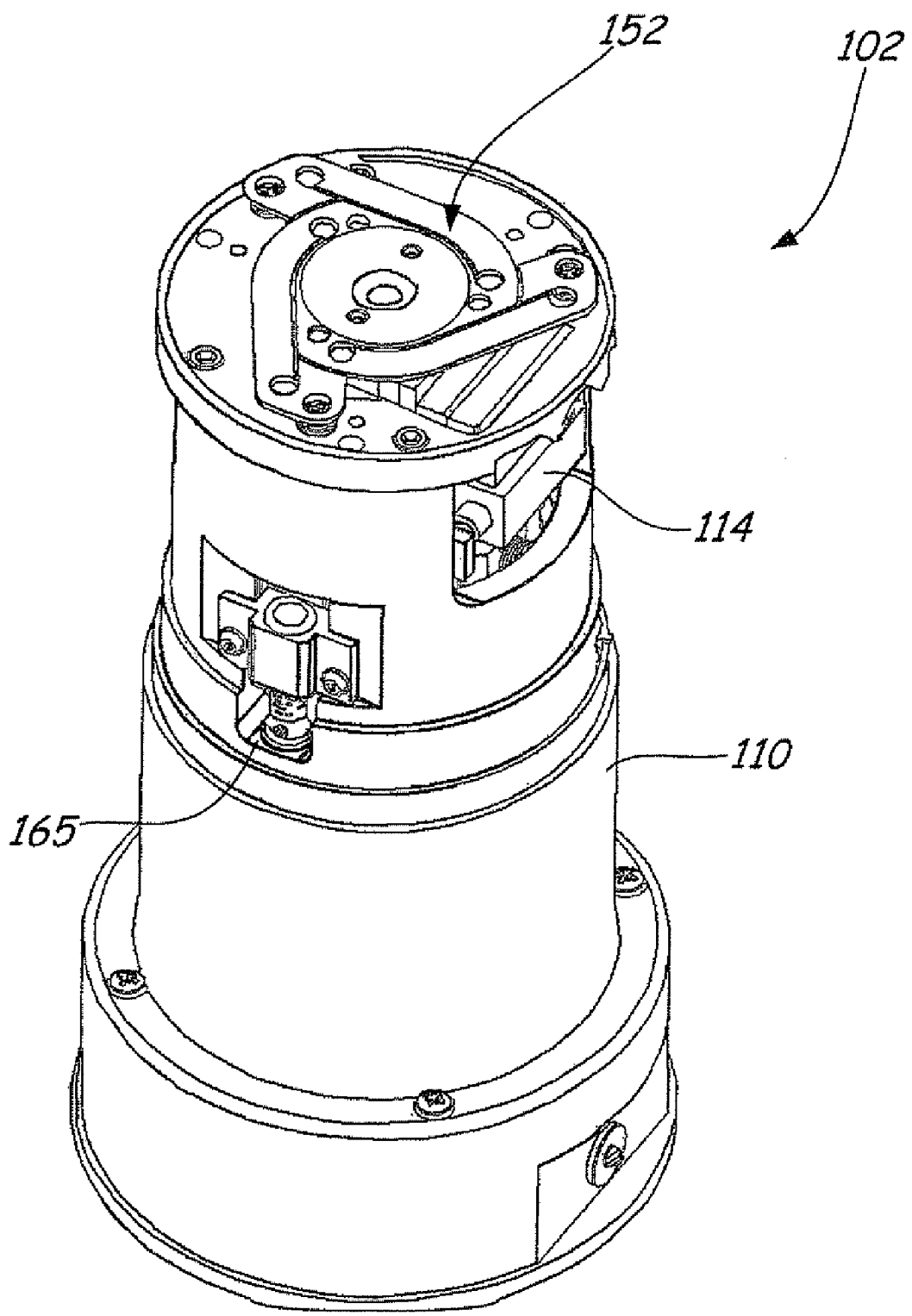
FIG. 12 illustrates a perspective view of an optical testing device with its kinematic interface removed in accordance with an embodiment of the present invention.

FIG. 12 illustrates a perspective view of optical testing device 102 with kinematic interface 112 (FIGS. 2 and 3) removed. FIG. 12 illustrates the placement of flex mechanism 152 with respect to main body 110 and optical imaging system 114. In addition, FIG. 12 illustrates a motor 165 configured to linearly translate optical imaging system 114 for focusing of optical testing device 102.

Figure 13:
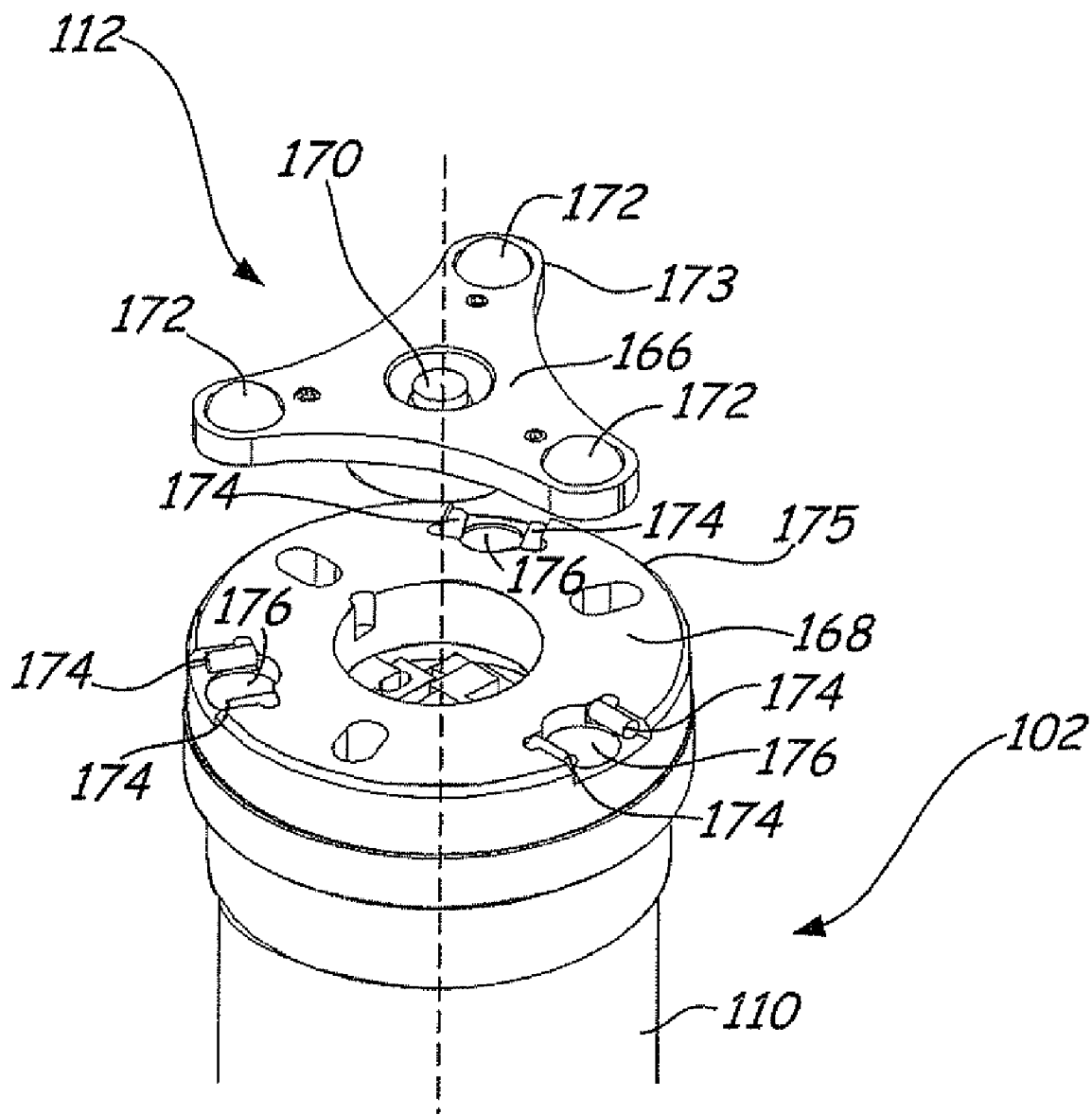
FIG. 13 illustrates an exploded perspective view of a kinematic interface in accordance with an embodiment of the present invention.

FIG. 13 illustrates an exploded perspective view of kinematic interface 112 in accordance with an embodiment of the present invention. As illustrated, kinematic interface 112 is a kinematic mount that is connected to main body 110 of optical testing device 102 and configured to receive, retain, and fixedly secure an optical specimen 105 (FIG. 1) for inspection without any further manipulation. Kinematic interface 112 is positioned proximal to optical imaging system 114 (FIG. 3). Kinematic Interface 112 includes an adapter 166 and an interface plate 168. Adapter 166 holds the optical specimen to be tested and rigidly fixes the optical specimen to main body 110 of optical testing device 102.

In accordance with an embodiment of the present invention, adapter 166 is interchangeable with other adapters such that kinematic interface 112 can accept various types of optical specimens. For example, to inspect fiber or fiber connector endfaces, each interchangeable adapter is configured to accept one of a standard fiber connector, a custom fiber connector and a bare fiber as used in the fiber optic industry. For example, different types of adapters can be made to accept different types of connectors, such as, an FC connector, an FCAPC (angled physical contact) connector, an ST connector, an SC connector, and a SCAPC (angled physical contact) connector. Each interchangeable adapter 166 is fitted with an optical specimen-specific insert 170. It should be noted that adapter 166 and insert 170 can be easily configured to receive various optical specimens outside of fiber optical specimens. For example, adapter 166 and insert 170 can be configured to receive lenses and arrays.

Adapter 166 and insert 170 mate to interface plate 168 through, but not by limitation, a six-point kinematic contact arrangement that utilizes at least three precision tooling balls 172. Precision tooling balls 172 are radially arranged and fixed about an outer edge 173 of adapter 166 and are seated in at least three "kinematic seats". "Kinematic seats" can include any type of configuration as long as the "kinematic seats" provide two points of contact. For example and as illustrated in FIG. 13, tooling balls 172 can be seated in pins 174. In another example, but not illustrated, tooling balls 172 can be seated in a v-shaped groove. In FIG. 13, pins 174 are fixed to interface plate 168. Tooling balls 172 and the "kinematic seats" are radially arranged about an outer edge 175 of kinematic interface 112. Magnets 176 are radially arranged and mounted to an outer edge 175 of interface plate 168 and impart an equivalent pull on tooling balls 172 to form a consistent load on the adapter 166. This configuration allows easy swapping between different types of adapters for receiving different types of optical specimens.

An interchangeable adapter 166 is precisely aligned during fabrication to ensure that the position of tooling balls 172 are within a predetermined tolerance of the nominal position of an optical specimen. Such alignment during fabrication of each adapter results in repeated positioning of an optical specimen that is less than 2 microns away from a prior position. In addition, interface plate 168 is aligned to main body 110 in accordance with optical axis 139.

Each interchangeable adapter 166 can also serve as an interface component for existing optical systems, such as polishing systems. For example, in one application, a fiber or fiber connector is mounted to a polishing system and can be tested by optical testing device 102 without disconnecting the fiber or fiber connector from the polishing mount. In this example, adapter 166 is fixed and aligned to the polishing mechanism and optical testing device 102 is joined to the polishing mechanism through interface plate 168. Such a configuration allows a user to inspect the endface of the fiber or fiber connector without removing the fiber or fiber connector from the polishing mechanism for positioning in kinematic interface 112. Instead, the fiber or fiber connector remains on the polishing mechanism and the portable properties of optical testing device 102 allow inspection of the endface of the fiber or fiber connector. It should be noted that polishing mechanisms are not the only type of optical processing system in which an optical specimen can remain attached while optical testing device 102 does an inspection. Other types of optical processing systems are within the scope of the present invention, such as cleaning mechanisms.

Although not specifically illustrated in FIGS. 1-13, optical testing device 102 performs a set of calibrations such that the inspection results of the microscope visual mode and the interferometric measurement mode are accurate. In order to calibrate optical testing device 102, a specially fabricated adapter is fitted with interface plate 168 of mount 112. The specially fabricated adapter includes a calibration specimen. The calibration specimen comprises a spherical piece of which the topography and surface quality is known. For example, the calibration specimen can be a lens or other three-dimensional or two-dimensional target. A two-dimensional target can be used to calibrate microscope distortion and other elements of microscope use, while a three-dimensional target can be used to calibrate elements of fringe images. Optical testing device 102 performs an inspection on the calibration specimen and the optical testing device is calibrated accordingly. In addition, optical testing device 102 also performs a phase-shift calibration such that reference mirror 118 is moved an appropriate distance that coincides with an appropriate phase-shift of the beam of light reflecting of the reference mirror.

Although the present invention has been described with reference to preferred embodiments, workers skilled in the art will recognize that changes may be made in form and detail without departing from the spirit and scope of the invention.

The invention claimed is:

1. A method of inspecting a surface of an optical component, the method comprising:
    providing a portable optical inspection device configured to receive and inspect an optical specimen while the optical specimen is attached to a mount of a different optical processing system, the portable optical inspection device having an optical imaging system housed in a main body that is translatable along an optical axis and is prevented from movement in any direction perpendicular to the optical axis;
    acquiring a magnified visual image of the surface of the optical specimen with the optical imaging system;
    performing a surface defect analysis on the magnified visual image of the optical specimen;
    acquiring at least one fringe pattern image of the surface of the optical specimen with the optical imaging system;
    performing a surface topography analysis on the fringe pattern image of the optical specimen; and
    outputting the surface defect analysis and the surface topography analysis to a user device.

2. The method of claim 1, wherein the different optical processing system comprises one of a polishing mechanism and a cleaning mechanism.

3. The method of claim 1, wherein performing the surface defect analysis on the magnified visual image comprises:
    determining a center point of the optical specimen;
    identifying defects on the surface of the optical specimen; and
    determining whether the defects on the surface of the optical specimen are acceptable defects for the optical specimen.

4. The method of claim 3, wherein determining whether the defects on the surface of the optical specimen are acceptable comprises:
    measuring a size of each defect; and
    comparing the size of each defect to an acceptable defect size, if the size of the defect is less than the acceptable defect size, then the defect is acceptable.

5. The method of claim 3, wherein determining whether the defects on the surface of the optical specimen are acceptable comprises:
    determining a location of each defect relative to the center point; and
    comparing the location of each defect to acceptable locations relative to the center point of the optical specimen, if the defect is in an acceptable location, then the defect is acceptable.

6. The method of claim 3, wherein identifying defects on the surface of the optical specimen comprises classifying each defect on the surface of the optical specimen.

7. The method of claim 1, wherein performing the surface topography analysis on the at least one fringe pattern image comprises:
    comparing a three-dimensional shape of the optical specimen to an acceptable three dimensional shape to determine if the three-dimensional shape of the optical specimen is acceptable.

8. The method of claim 7, further comprising determining a surface roughness of the optical specimen by comparing the surface roughness of the optical specimen to an acceptable surface roughness, if the surface roughness is less than the acceptable surface roughness, then the defect is acceptable.

9. The method of claim 7, wherein comparing the three-dimensional shape of the optical specimen to an acceptable three-dimensional shape comprises:
    measuring at least one of radius, apex offset and a fiber height; and
    comparing the at least one of radius, apex offset and fiber height with one of a radius, apex offset and fiber height of the acceptable three-dimensional shape.

10. The method of claim 1, wherein providing the portable optical inspection device comprises providing a six-point kinematic interface including an adapter and an interface plate, the adapter configured for receiving the optical specimen attached to the mount of the different optical processing system and the interface plate configured to receive the adapter, wherein the six-point kinematic interface secures the adapter in three degrees of translational movement and three degrees of rotational movement.

11. The method of claim 10, wherein the adapter is configured to receive a specific type of optical specimen and, therefore, the adapter is interchangeable with other adapters that receive other types of optical specimens.

12. The optical testing device of 10, wherein the adapter comprises a plurality of spheres arranged about the adapter and are configured to mate with a plurality of seats on the interface plate.

13. An optical testing device comprising:
    a main body;
    an optical axis;
    an optical imaging system housed in the main body that is translatable along an optical axis and is prevented from movement in any direction perpendicular to the optical axis, the optical imaging system having imaging components for acquiring a microscope visual image and for acquiring at least one interference fringe image of the surface of the optical specimen;

an interface connected to the main body and configured to receive and rigidly secure the optical specimen in alignment with the optical axis; and wherein the optical specimen is configured to simultaneously attach to a mount of a different optical processing system and to the main body of the optical testing device with the interface.

14. The optical testing device of claim 13, wherein the interface comprises an interface plate coupled to the main body and an adapter configured to receive a specific type of optical specimen and, therefore, the adapter is interchangeable with other adapters that receive other types of optical specimens.

15. The optical testing device of claim 13, wherein the different optical processing system comprises one of a polishing mechanism and a cleaning mechanism.

16. The optical testing device of claim 13, wherein the optical imagining system performs a surface defect analysis on the microscope visual image of the optical specimen, the surface defect analysis includes a determination of whether the defects on the surface of the optical specimen are acceptable defects.

17. The optical testing device of claim 13, wherein the optical imaging system performs a surface topography analysis on the at least one interference fringe image of the optical specimen, the surface topography analysis includes a comparison between a three-dimensional shape of the optical specimen and an acceptable three dimensional shape to determine if the three-dimensional shape of the optical specimen is acceptable.

* * * * *